(12) United States Patent
Perni et al.

(10) Patent No.: US 7,494,988 B2
(45) Date of Patent: Feb. 24, 2009

(54) INHIBITORS OF SERINE PROTEASES, PARTICULARLY HEPATITIS C VIRUS NS3 PROTEASE

(75) Inventors: Robert Perni, Marlborough, MA (US); John Court, Littleton, MA (US); Ethan O'Malley, Belmont, MA (US); Govinda Rao Bhisetti, Lexington, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 440 days.

(21) Appl. No.: 10/391,932

(22) Filed: Mar. 19, 2003

(65) Prior Publication Data

US 2003/0236242 A1 Dec. 25, 2003

Related U.S. Application Data

(63) Continuation of application No. PCT/US01/10367, filed on Mar. 29, 2001.

(60) Provisional application No. 60/198,330, filed on Apr. 18, 2000, provisional application No. 60/194,563, filed on Apr. 3, 2000.

(51) Int. Cl.
*A61K 31/396* (2006.01)
*A61K 31/397* (2006.01)
*C07D 205/04* (2006.01)
*C07D 203/08* (2006.01)

(52) U.S. Cl. .......................... 514/210.17; 514/210.17; 514/422; 548/953; 548/964

(58) Field of Classification Search ................ 548/953, 548/964; 514/210.17, 422
See application file for complete search history.

(56) References Cited

U.S. PATENT DOCUMENTS

| | | | |
|---|---|---|---|
| 6,265,380 B1 | 7/2001 | Tung et al. | |
| 6,608,067 B1 | 8/2003 | Tung et al. | |
| 6,617,309 B2 | 9/2003 | Tung et al. | |
| 6,900,238 B1 * | 5/2005 | Wong et al. | 514/423 |
| 6,909,000 B2 | 6/2005 | Farmer et al. | |
| 7,109,172 B2 | 9/2006 | Britt et al. | |
| 7,208,600 B2 | 4/2007 | Cottrell et al. | |
| 7,241,796 B2 | 7/2007 | Farmer et al. | |
| 7,273,885 B2 | 9/2007 | Pitlik et al. | |
| 7,365,092 B2 | 4/2008 | Cottrell et al. | |
| 7,378,422 B2 | 5/2008 | Perni et al. | |
| 2004/0077600 A1 | 4/2004 | Tung et al. | |
| 2004/0266731 A1 | 12/2004 | Tung et al. | |
| 2005/0090450 A1 | 4/2005 | Farmer et al. | |
| 2005/0119189 A1 | 6/2005 | Cottrell et al. | |
| 2005/0197299 A1 | 9/2005 | Babine et al. | |
| 2005/0215486 A1 | 9/2005 | Cottrell et al. | |
| 2006/0211629 A1 | 9/2006 | Britt et al. | |
| 2007/0161789 A1 | 7/2007 | Cottrell et al. | |
| 2007/0179167 A1 | 8/2007 | Cottrell et al. | |
| 2007/0292933 A1 | 12/2007 | Pitlik et al. | |
| 2008/0045480 A1 | 2/2008 | Farmer et al. | |
| 2008/0125376 A1 | 5/2008 | Cottrell et al. | |

FOREIGN PATENT DOCUMENTS

| | | |
|---|---|---|
| WO | WO 98/17679 | 4/1998 |
| WO | WO 99/50230 | 10/1999 |

OTHER PUBLICATIONS

U.S. Appl. No. 12/082,668 by John J. Court, et al., filed on Apr. 10, 2008.
U.S. Appl. No. 11/711,845 by Kevin M. Cottrell, et al., filed on Feb. 27, 2007.
U.S. Appl. No. 12/031,486, by Mark A. Murcko, et al., filed on Feb. 14, 2008.

* cited by examiner

*Primary Examiner*—Kamal A Saeed
*Assistant Examiner*—Janet L Coppins
(74) *Attorney, Agent, or Firm*—Susan C. Kelly

(57) ABSTRACT

The present invention relates to compounds that are useful as protease inhibitors, particularly as serine protease inhibitors, and more particularly as hepatitis C NS3 protease inhibitors. As such, they act by interfering with the life cycle of the hepatitis C virus and are also useful as antiviral agents. This invention also relates to pharmaceutical compositions comprising these compounds. The compounds and pharmaceutical compositions of this invention are particularly well suited for inhibiting HCV NS3 protease activity and consequently, may be advantageously used as therapeutic agents against the hepatitis C virus and other viruses that are dependent upon a serine protease for proliferation. This invention also relates to methods for inhibiting the activity of proteases, including hepatitis C virus NS3 protease and other serine proteases, using the compounds of this invention and related compounds.

22 Claims, No Drawings

1

INHIBITORS OF SERINE PROTEASES, PARTICULARLY HEPATITIS C VIRUS NS3 PROTEASE

This application is a continuation of pending International Application No. PCT/US01/10367 filed Mar. 29, 2001, which was publication Oct. 11, 2001 under PCT Article 21(2) in English as Publication No. WO 01/74768, which claims the benefit of U. S. Provisional Application No. 60/198,330, filed Apr. 18, 2000, and the benefit of U. S. Provisional Application No. 60/194,563, filed Apr. 3, 2000, the contents of these documents being incorporated herein.

TECHNICAL FIELD OF THE INVENTION

The present invention relates to compounds that are useful as protease inhibitors, particularly as serine protease inhibitors, and more particularly as hepatitis C NS3 protease inhibitors. As such, they act by interfering with the life cycle of the hepatitis C virus and are also useful as antiviral agents. This invention also relates to pharmaceutical compositions comprising these compounds. The compounds and pharmaceutical compositions of this invention are particularly well suited for inhibiting HCV NS3 protease activity and consequently, may be advantageously used as therapeutic agents against the hepatitis C virus and other viruses that are dependent upon a serine protease for proliferation. This invention also relates to methods for inhibiting the activity of proteases, including hepatitis C virus NS3 protease and other serine proteases, using the compounds of this invention and related compounds.

BACKGROUND OF THE INVENTION

Infection by hepatitis C virus ("HCV") is a compelling human medical problem and is now recognized as the causative agent for most cases of non-A, non-B hepatitis.

The hepatitis C virus is thought to infect chronically 3% of the world's population [A. Alberti et al., "Natural History of Hepatitis C," *J. Hepatology,* 31 (Suppl. 1), pp. 17-24 (1999)]. In the United States alone the infection rate is 1.8% or 3.9 million people [M. J. Alter, "Hepatitis C Virus Infection in the United States," *J. Hepatology,* 31 (Suppl. 1), pp. 88-91 (1999)]. Of all patients infected over 70% develop chronic infection. Chronic infection is a major cause cirrhosis and hepatocellular carcinoma. [D. Lavanchy, "Global Surveillance and Control of Hepatitis C," *J. Viral Hepatitis,* 6, pp. 35-47 (1999)]

While interferon-α therapy and more recently interferon-ribavirin combination therapy have been available for the treatment of hepatitis C infection sustained response rates tend to be low (<50%) and side effects tend to be severe [M. A. Walker, "Hepatitis C Virus: an Overview of Current Approaches and Progress," *DDT,* 4, pp. 518-529 (1999); and D. Moradpour et al., "Current and Evolving Therapies for Hepatitis C," *Eur. J. Gastroenterol. Hepatol.,* 11, pp. 1199-1202 (1999)]. There is a clear need for more effective and better tolerated therapies The HCV genome encodes a polyprotein of 3010-3033 amino acids [Q.-L. Choo, et al., "Genetic Organization and Diversity of the Hepatitis C Virus", *Proc. Natl. Acad. Sci. USA,* 88, pp. 2451-2455 (1991); N. Kato et al., "Molecular Cloning of the Human Hepatitis C Virus Genome From Japanese Patients with Non-A, Non-B Hepatitis", *Proc. Natl. Acad. Sci. USA,* 87, pp. 9524-9528 (1990); A. Takamizawa et al., "Structure and Organization of the Hepatitis C Virus Genome Isolated From Human Carriers", *J. Virol.,* 65, pp. 1105-1113 (1991)]. The HCV nonstructural (NS) proteins are presumed to provide the essential catalytic machinery for viral replication. The NS proteins are derived by proteolytic cleavage of the polyprotein [R. Bartenschlager et al., "Nonstructural Protein 3 of the Hepatitis C Virus Encodes a Serine-Type Proteinase Required for Cleavage at the NS3/4 and NS4/5 Junctions", *J. Virol.,* 67, pp. 3835-3844 (1993); A. Grakoui et al. "Characterization of the Hepatitis C Virus-Encoded Serine Proteinase: Determination of Proteinase-Dependent Polyprotein Cleavage Sites", *J. Virol.,* 67, pp. 2832-2843 (1993); A. Grakoui et al., Expression and Identification of Hepatitis C Virus Polyprotein Cleavage Products", *J. Virol.,* 67, pp. 1385-1395 (1993); L. Tomei et al., "NS3 is a serine protease required for processing of hepatitis C virus polyprotein", *J. Virol.,* 67, pp. 4017-4026 (1993)].

The HCV NS protein 3 (NS3) contains a serine protease activity that helps process the majority of the viral enzymes, and is thus considered essential for viral replication and infectivity. It is known that mutations in the yellow fever virus NS3 protease decreases viral infectivity [T. J. Chambers et al., "Evidence that the N-terminal Domain of Nonstructural Protein NS3 From Yellow Fever Virus is a Serine Protease Responsible for Site-Specific Cleavages in the Viral Polyprotein", *Proc. Natl. Acad. Sci. USA,* 87, pp. 8898-8902 (1990)]. The first 181 amino acids of NS3 (residues 1027-1207 of the viral polyprotein) have been shown to contain the serine protease domain of NS3 that processes all four downstream sites of the HCV polyprotein [C. Lin et al., "Hepatitis C Virus NS3 Serine Proteinase: Trans-Cleavage Requirements and Processing Kinetics", *J. Virol.,* 68, pp. 8147-8157 (1994)]

The HCV NS3 serine protease and its associated cofactor, NS4A, helps process all of the viral enzymes, and is thus considered essential for viral replication. This processing appears to be analogous to that carried out by the human immunodeficiency virus aspartyl protease, which is also involved in viral enzyme processing HIV protease inhibitors, which inhibit viral protein processing are potent antiviral agents in man, indicating that interrupting this stage of the viral life cycle results in therapeutically active agents. Consequently it is an attractive target for drug discovery.

Several potential HCV protease inhibitors have been described. PCT publications WO 00/09558, WO 00/09543, WO 99/64442, WO 99/07733, WO 99/07734, WO 99/50230 and WO 98/17679 each describe potential HCV NS3 protease inhibitors. Unfortunately, none of those inhibitors has yet begun clinical trials and there are no serine protease inhibitors available currently as anti-HCV agents.

Furthermore, the current understanding of HCV has not led to any other satisfactory anti-HCV agents or treatments. The only established therapy for HCV disease is interferon treatment. However, interferons have significant side effects [H. L. A. Janssen et al., "Suicide Associated with Alfa-Interferon Therapy for Chronic Viral Hepatitis," *J. Hepatol.,* 21, pp. 241-243 (1994); P. F. Renault et al., "Side effects of alpha interferon", *Seminars in Liver Disease* 9, pp. 273-277. (1989)] and induce long term remission in only a fraction (~25%) of cases [O. Weiland, "Interferon Therapy in Chronic Hepatitis C Virus Infection", *FEMS Microbiol. Rev.,* 14, PP. 279-288 (1994)]. Moreover, the prospects for effective anti-HCV vaccines remain uncertain.

Thus, there is a need for more effective anti-HCV therapies. Such inhibitors would have therapeutic potential as protease inhibitors, particularly as serine protease inhibitors, and more particularly as HCV NS3 protease inhibitors. Specifically, such compounds may be useful as antiviral agents, particularly as anti-HCV agents.

SUMMARY OF THE INVENTION

The present invention provides compounds, and pharmaceutically acceptable derivatives thereof, that are useful as protease inhibitors, particularly as serine protease inhibitors, and more particularly as HCV NS3 protease inhibitors. These compounds can be used alone or in combination with immunomodulatory agents, such as α-, β- or γ-interferons; other antiviral agents such as ribavirin and amantadine; other inhibitors of hepatitis C protease; inhibitors of other targets in the HCV life cycle including the helicase, polymerase, metalloprotease, or internal ribosome entry; or combinations thereof.

The present invention also provides methods for inhibiting proteases, particularly serine proteases, and more particularly HCV NS3 protease.

The present invention also provides pharmaceutical compositions comprising the compounds of this invention, as well as multi-component compositions comprising additional immunomodulatory agents, such as α-, β- or γ-interferons; other antiviral agents such as ribavirin and amantadine; other inhibitors of hepatitis C protease, inhibitors of other targets in the HCV life cycle including the helicase, polymerase, metalloprotease, or internal ribosome entry; or combinations thereof. The invention also provides methods of using the compounds of this invention, as well as other related compounds, for the inhibition of HCV.

DETAILED DESCRIPTION OF THE INVENTION

In order that the invention herein described may be more fully understood, the following detailed description is set forth. In the description, the following abbreviations are used:

| Designation | Reagent or Fragment |
|---|---|
| Alloc | allyl carbamate |
| Boc | tert-butyl carbamate |
| BOP | benzotriazol-1-yl-oxytris (dimethylamino) phosphonium hexafluorophosphate |
| CDI | carbonyldiimidazole |
| Cbz | benzyl carbamate |
| DCC | dicyclohexylcarbodiimide |
| DIC | di-iso-propylcarbodiimide |
| DIEA | diisopropylethylamine |
| DMA | dimethylacetamide |
| DMF | dimethylformamide |
| DPPA | diphenylphosphorylazide |
| DMSO | dimethylsulfoxide |
| EDC | 1-ethyl-3-(3-dimethylaminopropyl) carbodiimide HCl |
| Et | ethyl |
| Et$_2$O | diethyl ether |
| EtOAc | ethyl acetate |
| FMOC | 9-fluorenylmethoxycarbonyl |
| HOAt | 1-hydroxy-7-azabensotriazole |
| HOBt | 1-hydroxybenzotriazole |
| HOSu | N-hydroxysuccinamide |
| HPLC | high performance liquid chromatography |
| KOTMS | potassium trimethylsilanoate |
| NMP | N-methyl pyrrolidinone |
| ND | not determined |
| PPTS | pyridinium p-toluenesulfonate |
| PyBOP | benzotriazole-1-yl-oxytris-pyrrolidino-phosphonium hexafluorophosphate |
| PyBrop | bromo-tris-pyrrolidinophosphonium hexafluorophosphate |
| THF | tetrahydrofuran |
| THP | tetrahydropyran |
| TFA | trifluoroacetic acid |

The following terms are used herein:

Unless expressly stated to the contrary, the terms "—SO$_2$—" and "—S(O)$_2$—" as used herein refer to a sulfone or sulfone derivative (i.e., both appended groups linked to the S), and not a sulfinate ester.

The term "halo" or "halogen" refers to a radical of fluorine, chlorine, bromine or iodine. Preferred halogen radicals include fluorine and chlorine.

In chemical formulas, parentheses are used herein to indicate 1) the presence of more than one atom or group bonded to the same atom or group; or 2) a branching point in a chain (i.e., the group or atom immediately before the open parenthesis is bonded directly to the group or atom immediately after the closed parenthesis). An example of the first use is "N(R$^1$)$_2$" denoting two R$^1$ groups bound to the nitrogen atom. An example of the second use is "—C(O)R$^1$" denoting an oxygen atom and a R$^1$ bound to the carbon atom, as in the following structure:

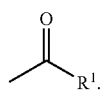

According to one embodiment, the invention provides a compound of the formula (I):

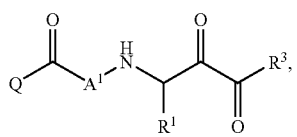

wherein:

R$^1$ is selected from (C$_1$-C$_6$)-straight or branched alkyl, or (C$_2$-C$_6$)-straight or branched alkenyl or alkynyl, wherein up to 4 hydrogen atoms in R$^1$ are optionally and independently replaced with a halogen; and wherein any hydrogen atom bound to any terminal carbon atom in R$^1$ is optionally and independently replaced with —SH or —OH;

R$^3$ is selected from

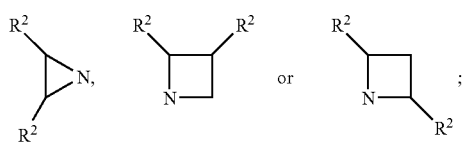

wherein each $R^2$ is independently selected from —$R^{11}$, —Ar, —O—$R^{11}$, —O—Ar, —O—$R^{11}$—Ar, —$R^{11}$—C(O)—$R^{11}$, —N($R^{11}$)$_2$, —N($R^{11}$)—C(O)O—$R^{11}$, —N($R^{11}$)—C(O)O—$R^{11}$—Ar, —C(O)O—$R^{11}$, —O—C(O)—N($R^{11}$)$_2$, halo, —CN, —NO$_2$, —$R^{11}$—C(O)—$R^{11}$, —$R^{11}$—C(O)O—$R^{11}$, —C(O)—N($R^{11}$)$_2$, —C(O)—N($R^{11}$)—Ar, —S(O)$_2$—$R^{11}$, or —S(O)$_2$—N($R^{11}$)$_2$;

wherein up to 2 hydrogen atoms in $R^2$ are optionally and independently replaced with a different moiety selected from —$R^{11}$, —Ar, —O—$R^{11}$, —O—Ar, —O—$R^{11}$—Ar, —$R^{11}$—C(O)—$R^{11}$, —NH—($R^{11}$)$_2$, —N($R^{11}$)—C(O)O—$R^{11}$, —N($R^{11}$)—C(O)O—$R^{11}$—Ar, —C(O)O—$R^{11}$, —O—C(O)—N($R^{11}$)$_2$, halo, —CN, —NO$_2$, —$R^{11}$—C(O)—$R^{11}$, —$R^{11}$—C(O)O—$R^{11}$, —O—C(O)—$R^{11}$, —C(O)—N($R^{11}$)$_2$, —C(O)—N($R^{11}$)—Ar, —N($R^{11}$)—C(O)—$R^{11}$, —$R^{11}$—C(O)—N($R^{11}$)$_2$, —S(O)$_2$—$R^{11}$, or —S(O)$_2$—N($R^{11}$)$_2$;

wherein each $R^{11}$ is independently selected from hydrogen, ($C_1$-$C_6$)-straight or branched alkyl or ($C_2$-$C_6$)-straight or branched alkenyl or alkynyl; and wherein up to 3 hydrogen atoms in said alkyl, alkenyl or alkynyl are optionally and independently replaced with halo;

each Ar is a monocyclic, bicyclic or tricyclic ring system wherein in said ring system:
(a) each ring is independently partially unsaturated or fully saturated;
(b) each ring comprises 3 to 7 ring atoms independently selected from C, N, O or S;
(c) no more than 4 ring atoms in Q are selected from N, O or S; and
(d) any S is optionally replaced with S(O) or S(O)$_2$;

wherein up to 3 hydrogen atoms in each Ar is optionally and independently replaced with a moiety selected from —$R^{11}$, —Ar, —O—$R^{11}$, —O—Ar, —N($R^{11}$)$_2$, —N($R^{11}$)—Ar, —C(O)O$R^{11}$, —C(O)O—Ar, —C(O)—N($R^{11}$)$_2$, —O—C(O)—N($R^{11}$)$_2$, —CN, —NO$_2$, —S$R^{11}$, or —S—Ar; and wherein when a hydrogen atom in Ar is replaced with a first moiety comprising Ar, said first moiety is not substituted with a second moiety comprising Ar;

$A^1$ is selected from a bond, —NH—C($R^4$)—C(O)—, or

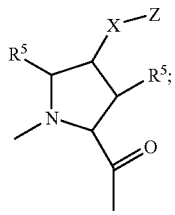

wherein X is selected from a bond, —O—, —NR—, —C(R)$_2$—, —C(O)—, —C(R)$_2$—C(R)$_2$—, —C(R)$_2$—C(R)$_2$—C(R)$_2$—, —C(R)=C(R)—, —CH(R)—O—, —C(R)—N(R)—, —C(R)$_2$—C(O)—, —O—C(R)$_2$—, —N(R)—C(R)$_2$—, —O—C(O)—, —N(R)—C(O)—, —C(O)—C(R)$_2$—, —C(O)—N(R)—, —C(O)—O—, —O—N(R)—, —N(R)—O—, —N(R)—N(R)—, or —N=N—; wherein each R is independently selected from —$R^{11}$, —Ar, —$R^{11}$—Ar, —C(O)O—$R^{11}$, —C(O)—N($R^{11}$)$_2$, —O—$R^{11}$, —O—Ar, halo, —CN, —NO$_2$, —N($R^{11}$)$_2$, —N($R^{11}$)—Ar, —S(O)$_2$—$R^{11}$, or —S(O)$_2$—N($R^{11}$)$_2$;

Z is selected from —$R^{11}$, —Ar, or —$R^{11}$—Ar;

$R^4$ is selected from —$R^{11}$, —Ar, —$R^{11}$—Ar, —C(O)O—Ar, or —O—C(O)—N($R^{11}$)$_2$, wherein up to 3 hydrogen atoms in $R^4$ are optionally and independently replaced with a different moiety selected from —$R^{11}$, —Ar, —O—$R^{11}$, —O—Ar, —O—$R^{11}$—Ar, —$R^{11}$—C(O)—$R^{11}$, —N—($R^{11}$)$_2$, —N($R^{11}$)—C(O)O—$R^{11}$, —C(O)—N($R^{11}$)$_2$, —N($R^{11}$)—C(O)O—$R^{11}$—Ar, —C(O)O—$R^{11}$, —O—C(O)—N($R^{11}$)$_2$, halo, —CN, —NO$_2$, —$R^{11}$—C(O)O—$R^{11}$, —S(O)$_2$—$R^{11}$, or —S(O)$_2$—N($R^{11}$)$_2$;

each $R^5$ is independently selected from —$R^{11}$, —Ar, —C(O)O—$R^{11}$, —C(O)O—Ar, —O—C(O)—N($R^{11}$)$_2$, —O—C(O)—N($R^{11}$)—Ar, —C(O)—N($R^{11}$)$_2$, —C(O)—N($R^{11}$)—Ar, —O—$R^{11}$, halo, —CN, —NO$_2$, —N(($R^{11}$)$_2$ or —S(O)$_2$—$R^{11}$;

or wherein —X-Z and one $R^5$ are taken together with the carbon atoms to which they are respectively bound to form a 5 to 7-membered ring comprising 0 to 3 heteroatoms independently selected from O, N, or S;

Q is selected from —O$R^6$, —N($R^6$)$_2$, $R^{11}$, —$R^{11}$—O—$R^{11}$, —$R^{11}$—NH$_2$, —Ar, $A^3$—NH—C($R^7$)—, or —$A^3$; wherein each $R^6$ is independently selected from $R^{11}$, —$R^{11}$—O—$R^{11}$, —$R^{11}$—NH$_2$, —$R^{11}$—Ar, or —Ar; and $R^7$ is selected from —$R^{11}$ or —Ar;

$A^3$ is selected from $R^6$, $R^8$—C(O)—, $R^8$—S(O)$_2$—, $R^6$—C(O)—NH—C($R^6$)—C(O)— or $R^6$—NH—C($R^6$)—C(O)—; and $R^8$ is selected from —$R^6$, —O$R^6$, or —N($R^6$)$_2$.

The term "ring atom", as used herein, refers to a backbone atom that makes up the ring. Such ring atoms are selected from C, N. O or S and are bound to 2 or 3 other such ring atoms (3 in the case of certain ring atoms in a bicyclic ring system). The term "ring atom" does not include hydrogen.

According to one preferred embodiment, Q is $A^3$—NH—CH($R^7$)— and $A^3$ is selected from $R^6$—C(O)—NH—CH($R^6$)—C(O)—, $R^8$—C(O)— or $R^8$—S(O)$_2$—. More preferred is when Q is $A^3$—NH—CH(CH(CH$_3$)$_2$)—; $A^3$ is Ar—C(O)—NH—CH(CH(CH$_3$)$_2$)—C(O)—, $R^6$—O—C(O)—, $R^6$—O—S(O)$_2$—, or $R^6$—NH—C(O)—; and $R^6$ is $R^{11}$—, Ar—$R^{11}$— or Ar—. Even more preferred is when Q is selected from:

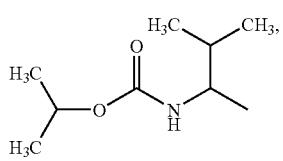

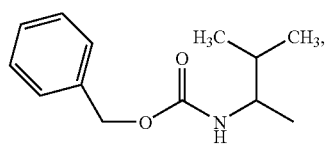

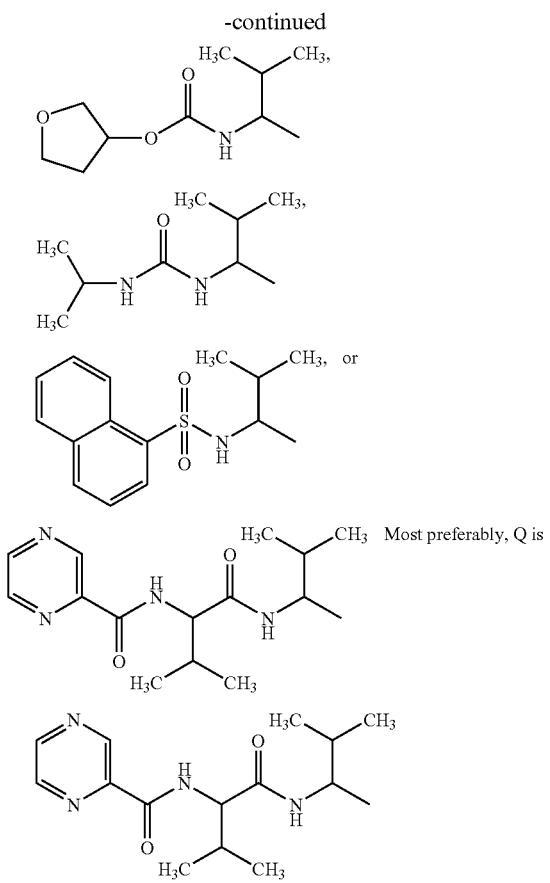

According to another preferred embodiment, $A^1$ is wherein X is —O—C(O)— or a bond; Z is hydrogen or Ar; one $R^5$ is hydrogen and the other $R^5$ is selected from —$R^{11}$, —Ar, —C(O)O—$R^{11}$, —C(O)O—Ar, —O—C(O)—NH ($R^{11}$); —O—C(O)—NH—Ar, —C(O)—NH($R^{11}$), —C(O)—NH—Ar; or wherein X, Z and one $R^5$ are taken together to form an unsubstituted or oxo-substituted cyclopentyl moiety. Even more preferred is when $A^1$ is selected from:

, wherein $R^{11}$ is not hydrogen.

Most preferably, $A^1$ is

According to another preferred embodiment, $R^1$ is a straight chain alkyl moiety. Even more preferred is when $R^1$ is n-propyl.

In yet another preferred embodiment, in the $R^3$ moiety, one $R^2$ is hydrogen and the other $R^2$ moiety is selected from $R^{11}$, C(O)—O—$R^{11}$, Ar or —OAr. More preferred is when the second $R^2$ moiety is selected from hydrogen, methyl, C(O) OH, C(O)OCH$_3$, C(O)OC(CH$_3$)$_3$, phenyl or phenoxy.

The most preferred compounds of the present invention have the formula (II):

(II)

Some specific preferred compounds of formula (II) are listed in the table below.

| Cmpd | $R^3$ |
|---|---|
| 1 | N-aziridine-C(O)OCH$_3$ |
| 2 | N-aziridine-C(O)OH |
| 3 | N-aziridine-C(O)OC(CH$_3$)$_3$ |
| 4 | N-aziridine |
| 5 | N-aziridine-CH$_3$ |
| 6 | N-aziridine-phenyl |
| 7 | N-azetidine |
| 8 | N-azetidine-C(O)OH |
| 9 | N-azetidine-O-phenyl |

Those of skill in the art will realize that certain combinations of moiety choices for variables in the generic structures set forth throughout this application will produce chemically unstable or unfeasible compounds. Such compounds are not intended to be part of the present invention.

The present invention provides compounds that are useful as protease inhibitors, particularly as serine protease inhibitors, and more particularly as HCV NS3 protease inhibitors. As such, they act by interfering with the life cycle of the HCV virus and other viruses that are dependent upon a serine protease for proliferation. Therefore, these compounds are useful as antiviral agents.

The compounds of this invention may contain one or more asymmetric carbon atoms and thus may occur as racemates and racemic mixtures, single enantiomers, diastereomeric mixtures and individual diastereomers. All such isomeric forms of these compounds are expressly included in the present invention. Each stereogenic carbon may be of the R or S configuration, unless specifically indicated.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a mammal or for use in affinity chromatography applications). Typically, such compounds are stable at a temperature of 40° C. or less, in the absence of moisture or other chemically reactive conditions, for at least a week.

The compounds of this invention may be synthesized using conventional techniques. Advantageously, these compounds are conveniently synthesized from readily available starting materials.

As used herein, the compounds of this invention are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention.

Accordingly, this invention also provides prodrugs of the compounds of this invention, which are derivatives that are designed to enhance biological properties such as oral absorption, clearance, metabolism or compartmental distribution. Such derivations are well known in the art.

As the skilled practitioner realizes, the compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The term "protected" refers to when the designated functional group is attached to a suitable chemical group (protecting group). Examples of suitable amino protecting groups and protecting groups are described in T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); L. Paquette, ed. *Encyclopedia of Reagents for Organic Synthesis*, John Wiley and Sons (1995) and are exemplified in certain of the specific compounds used in this invention.

Particularly favored derivatives and prodrugs are those that increase the bioavailability of the compounds of this invention when such compounds are administered to a mammal (e.g., by allowing an orally administered compound to be more readily absorbed into the blood), have more favorable clearance rates or metabolic profiles, or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formula (I).

Pharmaceutically acceptable salts of the compounds of this invention include those derived from pharmaceutically acceptable inorganic and organic acids and bases. Examples of suitable acid salts include acetate, adipate, alginate, aspartate, benzoate, benzene-sulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., calcium and magnesium), salts with organic bases, such as dicyclohexylamine salts, N-methyl-D-glucamine, salts with amino acids such as arginine and lysine, ammonium and N-($C_{1-4}$ alkyl)$_4^+$ salts.

This invention also envisions the quaternization of any basic nitrogen-containing groups of the compounds disclosed herein with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products may be obtained by such quaternization.

In general, compounds of formula (I) are obtained via methods illustrated in the Examples. As can be appreciated by the skilled artisan however the synthetic schemes set forth herein are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

Without being bound by theory, we believe that the compounds of this invention interact either covalently or noncovalently with the active site of the HCV NS3 protease and other serine proteases, inhibiting the ability of such an enzyme to cleave natural or synthetic substrates. Noncovalent interactions are advantageous in that they impart relatively greater specificity of inhibition and will not inhibit other undesirable targets, e.g. cysteine proteases. These compounds will therefore have a greater therapeutic index when administered to mammals than covalent protease inhibitors, which can interact with a wide range of proteases and cause undesirable toxic effects. In contrast, covalent interactions are advantageous in that they impart greater inhibitory potency allowing lower doses may be administered and thus ameliorating any lack of specificity problems.

The compounds of this invention may be assayed for inhibitory activity using HCV NS3 protease as the target enzyme (preferably with the addition of HCV NS4A) and various substrates. These assays are described in detail in WO 98/17679 (pages 103-105), the disclosure of which is herein incorporated by reference.

The novel compounds of the present invention are excellent inhibitors of proteases, particularly serine proteases, and more particularly HCV NS3 protease inhibitors. Accordingly, these compounds are capable of targeting and inhibiting proteases, particularly serine proteases, and more particularly HCV NS3 proteases. As such, these compounds interfere with the life cycle of viruses, including HCV and are thus useful as antiviral agents. Inhibition can be measured by various methods such as the methods of Example 3.

The term "antiviral agent" refers to a compound or drug which possesses viral inhibitory activity. Such agents include reverse transcriptase inhibitors (including nucleoside and non-nucleoside analogs) and protease inhibitors. Preferably the protease inhibitor is a HCV protease inhibitor.

The term "treating" as used herein refers to the alleviation of symptoms of a particular disorder in a patient or the improvement of an ascertainable measurement associated with a particular disorder. As used herein, the term "patient" refers to a mammal, including a human.

Thus, according to another embodiment this invention provides pharmaceutical compositions comprising a compound of formula (I) or a pharmaceutically acceptable salt thereof; an additional agent selected from an immunomodulatory agent, such as $\alpha$-, $\beta$-, or $\gamma$-interferon; other antiviral agents, such as ribavarin or amantadine; other inhibitors of HCV protease; inhibitors of other targets in the HCV life cycle such as helicase, polymerase, or metalloprotease inhibitors, or combinations thereof; and any pharmaceutically acceptable carrier, adjuvant or vehicle.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d$\alpha$-tocopherol, polyethyleneglycol 1000 succinate, or TPGS, surfactants used in pharmaceutical dosage forms such as Tweens or other similar polymeric delivery matrices, serum proteins, such as human serum albumin, gelatin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polylacetic acid, ployacetic polyglycollic acid, citric acid, cellulose-based substances, such as HPC and HPMC, polyethylene glycol, sodium carboxymethylcellulose, polyacrylates, waxes, polyethylene-polyoxypropylene-block polymers, polyethylene glycol, wool fat. Cyclodextrins such as $\alpha$-, $\beta$-, and $\gamma$-cyclodextrin, or chemically modified derivatives such as hydroxyalkylcyclodextrins, including 2- and 3-hydroxypropyl-$\beta$-cyclodextrins, or other solubilized derivatives may also be advantageously used to enhance delivery of compounds of formula (I).

The pharmaceutical compositions of this invention may be administered orally, parenterally, by inhalation spray, topically, rectally, nasally, buccally, vaginally or via an implanted reservoir. We prefer oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as those described in Pharmacopeia Helvetica (Ph. Helv.) or a similar alcohol, or carboxymethyl cellulose or similar dispersing agents which are commonly used in the formulation of pharmaceutically acceptable dosage forms such as emulsions and/or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose, corn starch, dicalcium phosphate and microcrystalline cellulose (Avicel). Lubricating agents, such as magnesium stearate and talc, are also typically added. For oral administration in a capsule form, useful diluents include lactose, dried corn starch and TPGS, as well as the other diluents used in tablets. For oral administration in a soft gelatin capsule form (filled with either a suspension or a solution of a compound of this invention), useful diluents include PEG400, TPGS, propylene glycol, Labrasol, Gelucire, Transcutol, PVP and potassium acetate. When aqueous suspensions are administered orally, the active ingredient is combined with emulsifying and suspending agents, such as sodium CMC, methyl cellulose, pectin and gelatin. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax, gelatin, glycerin and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, stearic acid, cetyl stearate, cetyl alcohol, lanolin, magnesium hydroxide, kaolin and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters, wax, cetyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Most preferred are pharmaceutical compositions which can orally administered.

Dosage levels of between about 0.01 and about 100 mg/kg body weight per day, preferably between about 0.5 and about 75 mg/kg body weight per day of the protease inhibitor compounds described herein are useful in a monotherapy for the prevention and treatment of antiviral, particularly anti-HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of formula (I) and one or more additional therapeutic or prophylactic agents, both the compound and the additional agent should be present at dosage-levels of between about 10 to 100%, and more preferably between about 10 to 80% of the dosage normally administered in a monotherapy regimen.

According to another alternate embodiment, the pharmaceutical compositions of this invention may additionally comprise other inhibitors of HCV protease other than those of formula (I).

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

According to another embodiment of this invention provides methods of inhibiting serine protease activity in mammals by administering a compound of the formula (I). Preferably, the serine protease is HCV NS3.

In an alternate embodiment, this invention provides methods of decreasing serine protease activity, preferably HCV NS3 protease activity, in a mammal comprising the step of administrating to said mammal any of the pharmaceutical compositions and combinations described above. If the pharmaceutical composition comprises only a compound of this invention as the active component, such methods may additionally comprise the step of administering to said mammal an agent selected from an immunomodulatory agent, an antiviral agent, a HCV protease inhibitor, or an inhibitor of other targets in the HCV life cycle as a separate dosage form. Such additional agent may be administered to the mammal prior to, concurrently with, or following the administration of the HCV inhibitor composition.

In an alternate preferred embodiment, the methods, compositions and combinations described above are useful for inhibiting viral replication in a mammal. Such methods are useful in treating or preventing, for example, viral diseases, such as HCV.

The compounds set forth herein may also be used as laboratory reagents. The compounds of this invention may also be used to eliminate or reduce viral contamination, preferably HCV contamination, of materials and therefore reduce the risk of viral infection of laboratory or medical personnel or patients who come in contact with such materials. These materials include, but are not limited to, biological materials, such as blood, tissue, etc; surgical instruments and garments; laboratory instruments and garments; and blood collection apparatuses and materials.

In order that this invention be more fully understood, the following examples are set forth. These examples are for the purpose of illustration only and are not to be construed as limiting the scope of the invention in any way.

General Materials and Methods

Compounds 1 through 7 were prepared using the synthesis scheme 1, depicted below, with appropriate modifications.

Numerous amino acids for use in the synthesis of peptidyl and peptidomimetic compounds of this invention may be purchased commercially from, for instance, Sigma Chemical Company or Bachem Feinchemikalien AG (Switzerland). Amino acids that are not commercially available can be made by known synthetic routes ("Kinetic Resolution of Unnatural and Rarely Occurring Amino Acids: Enantioselective Hydrolysis of N-Acyl Amino Acids Catalyzed by Acylase I", Chenault, H. K. et. al., *J. Am. Chem. Soc.* 111, 6354-6364 (1989) and references cited therein; "Synthesis of β-γ-Unsaturated Amino Acids by the Strecker Reaction, Greenlee, W. J., *J. Org. Chem.* 49, 2632-2634 (1984); "Recent Stereoselective Synthetic Approaches to Beta-amino Acids", Cole, D. *Tetrahedron* 50: 9517 (1994); "The Chemistry of Cyclic Alpha Imino Acids", Mauger, A. B; Volume 4 of "Chemistry and Biochemistry of Amino Acids, Peptides, and Proteins", Weinstein, B. editor, Marcel Dekker (1977); "Recent Progress in the Synthesis and Reactions of Substituted Piperidines", Org. Prep. Procedure Int. 24, 585-621 (1992), all of which are incorporated herein by reference).

Certain compounds of formula (I) may be synthesized from amino acids by procedures which are well known in the art of peptide and organic chemical synthesis. Examples of such syntheses are generally set forth in Bodanszky and Bodanszky, "The Practice of Peptide Synthesis", Springer-Verlag, Berlin, Germany (1984), "The Peptides", Gross and Meinhofer, eds; Academic Press, 1979, Vols. I-III, and Stewart, J. M. and Young, J. D., "Solid Phase Peptide Synthesis, Second Edition", Pierce Chemical Company, Rockford, Ill. (1984); and "Recent Advances in the Generation of Molecular Diversity", Moos, W. H., Green, G. D. and Pavia, M. R. in "Annual Reports in Medicinal Chemistry, Vol. 28" pp. 315-324; Bristol, J. A., ed.; Academic Press, San Diego, Calif. (1993), all of which are incorporated herein by reference.

Typically, for solution phase synthesis of peptides, the α-amine of the amino acid to be coupled is protected by a urethane such as Boc, Cbz, Fmoc or Alloc while the free carboxyl is activated by reaction with-a carbodiimide such as DCC, EDC, or DIC, optionally in the presence of a catalyst such as HOBT, HOAt, HOSu, or DMAP. Other methods, which proceed through the intermediacy of activated esters, acid halides, enzyme-activated amino acids and anhydrides including phosphonium reagents such as BOP, Py-BOP, N-carboxy-anhydrides, symmetrical anhydrides, mixed carbonic anhydrides, carbonic-phosphinic and carbonic-phosphoric anhydrides, are also suitable. After the peptide has been formed, protecting groups may be removed by methods described in the references listed above, such as by hydrogenation in the presence of a palladium, platinum or rhodium catalyst, treatment with sodium in liquid ammonia, hydrochloric, hydrofluoric, hydrobromic, formic, trifluoromethanesulfonic, or trifluoroacetic acid, secondary amines, fluoride ion, trimethylsilyl halides including bromide and iodide, or alkali. Automation of the synthetic process, using techniques such as those set forth above, can be accomplished by use of commercially available instrumentation, including but not limited to the Advanced Chemtech 357 FBS and 496 MOS; Tecan CombiTec, and Applied Biosystems 433A among others. Specific application of these methods and their equivalents, depending upon the target compound, will be apparent to those skilled in the art. Modifications of chemical processes and choice of instrumentation is within the skill of the ordinary practitioner.

Although the scheme depicted below indicate particular stereochemistry for certain groups, it should be apparent to those of skill in the art that the synthesis schemes may be modified to allow for the use of those certain groups having the opposite stereochemistry. Therefore, the indication of stereochemistry in these scheme is not intended to limit the depicted synthesis to any particular stereochemistry of any intermediate or final product.

EXAMPLE 1

Synthesis of Compound 1

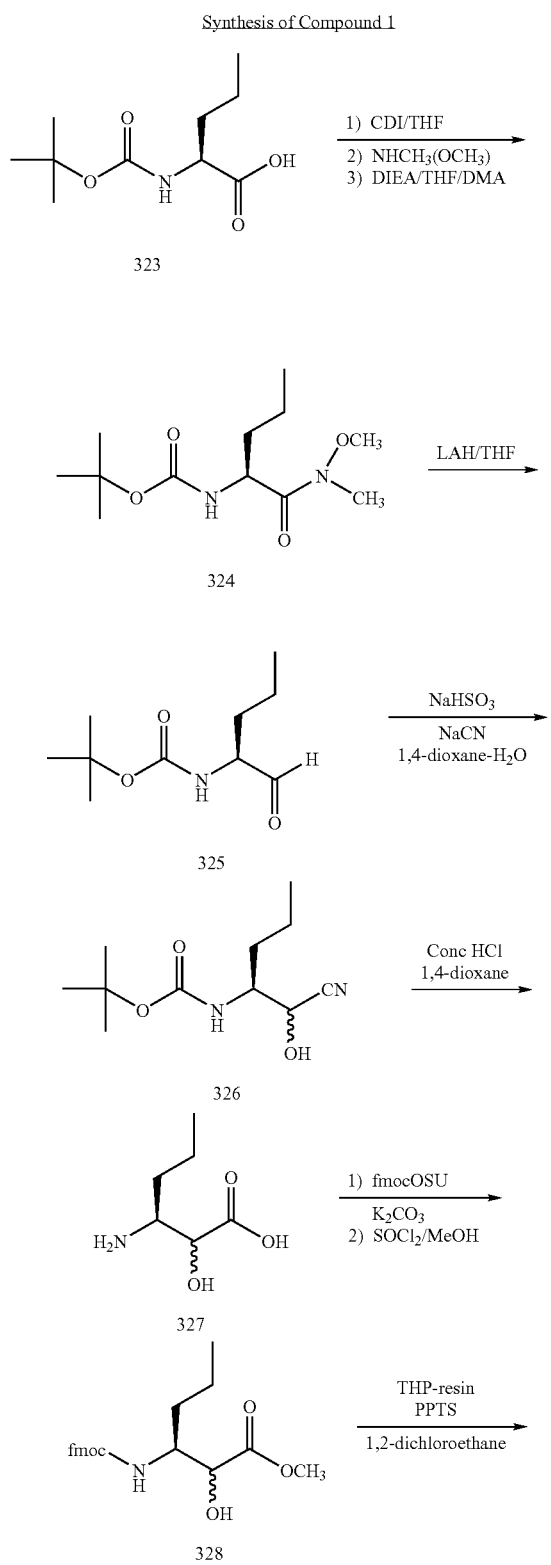

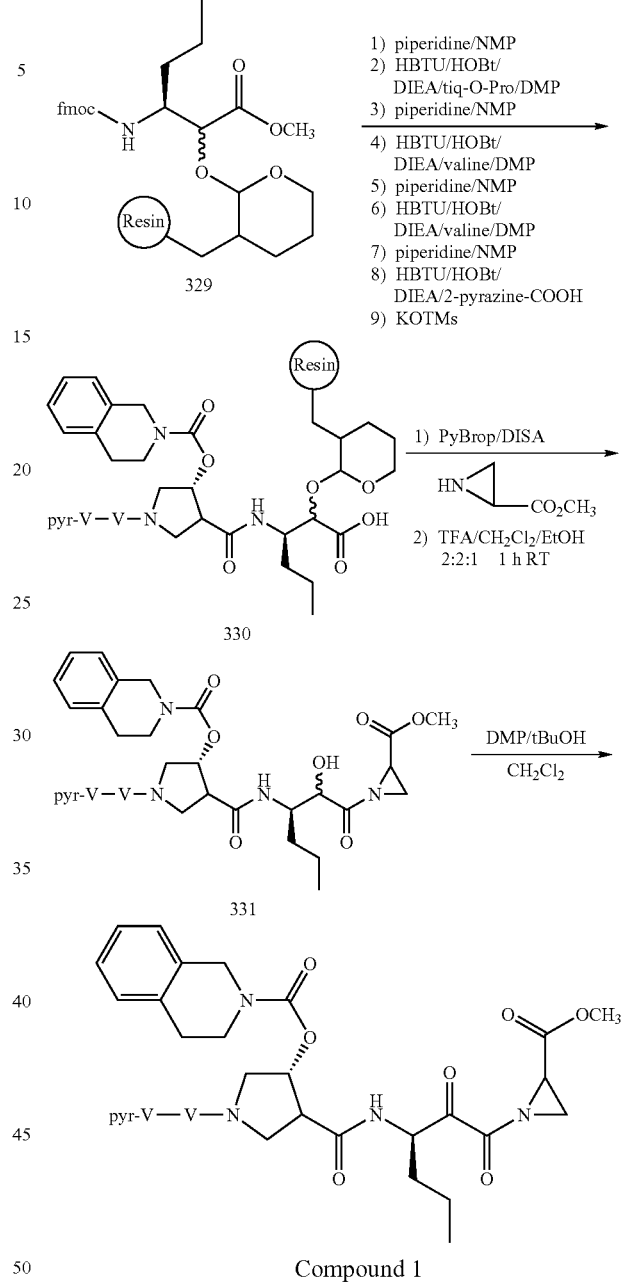

Compound 1

Step A. Synthesis of 324. To a solution of the BOC-amino acid 323 (25 g) in THF (250 mL) was added in portions, solid carbonyldiimidazole (CDI) (22.4 g). After 0.5 h a mixture of N-methyl-N-methoxyamine hydrochloride in DMA/DIEA (30 mL) was added and the resulting mixture was stirred at room temperature overnight. The reaction was washed by adding water (250 mL) and Et₂O/EtOAc (1:1, 500 mL) and then back-extracted once. The organic portion was washed with 0.5 N HCl, followed by brine and dried over sodium sulfate. The mixture was then filtered and the filtrate was concentrated in vacuo to afford 324 as a yellow oil (20 g).

Step B. Synthesis of 325. To a suspension of lithium aluminum hydride (LAH) in dry THF was added a solution of 324 (22.6 g) in THF (350 mL) over 100 minutes. The resulting solution was stirred for 1.5 h. The reaction was quenched by the addition of EtOAc (200 mL) followed by saturated sodium bitartrate (100 mL). The mixture was then stirred for 20 minutes while warming to room temperature. The layers were separated and the aqueous layer was extracted with EtOAc (2×). The organic layer was then concentrated in vacuo to remove THF and the resulting oil was re-dissolved in EtOAc. After washing with 0.5 N aqueous HCl and brine (3×), the solution was dried over magnesium sulfate. Filtration followed by concentration in vacuo afforded 325 as a yellow oil (17.1 g).

Step C. Synthesis of 326. To a solution of sodium bisulfite (10.55 g) in water (400 mL) at 0° C. was added a solution of 325 (17.1 g) in 1,4-dioxane (100 mL). The solution was then removed from the ice bath was stirred for 5 minutes. The solution was placed back in the ice bath and a solution of sodium cyanide (4.92 g) in water (40 mL) was added. The resulting mixture was then removed from the ice bath and allowed to warm to ambient temperature. Stirring was continued overnight. The reaction was then extracted with EtOAc. The EtOAc extract was dried over magnesium sulfate, filtered and concentrated in vacuo to afford 326 as a viscous yellow oil (19.6 g).

Step D. Synthesis of 327. A mixture of 326 (19.6 g) in concentrated hydrochloric acid (140 mL) was refluxed for 6 hours. After concentration in vacuo at 80° C. the product was redissolved in water. The aqueous solution was frozen and lyophilized to give 1 as a brown sticky solid (15.5 g)

Step E. Synthesis of 328. To a solution of 327 (5.8 g) in water (100 mL) was added potassium carbonate followed 1,4-dioxane. FMOC-OSU was added to the reaction in one portion. The reaction was stirred at ambient temperature overnight. Diethyl ether was added and the insoluble material was filtered. The bilayer filtrate was separated and the aqueous layer was washed with diethyl ether (2×) and acidified to pH 2 with 6N HCl. The solution was extracted with EtOAc (2×). The combined extracts were dried over magnesium sulfate, filtered and concentrated in vacuo to yield an off white amorphous foam. The foam was dissolved in methanol (44 mL) at 0° C. Thionyl chloride (9.9 g) was added dropwise, the reaction was allowed to warm to room temperature and stirred overnight. The resulting white solid was collected and the filtrate was concentrated to give a second crop of precipitate. The precipitate was collected and the combined solids were washed with diethyl ether and dried under high vacuum. The resulting solid was chromatographed on silica gel (eluting with 0 to 8% methanol in dichloromethane to afford 328 as a tan oil (6.84 g).

Step F. Synthesis of 329. A mixture of 328 (4.24 g), THP resin (5.47 g) and PPTS (3.37 g) was spun in an oil bath at 80° C. overnight. The resin was filtered off, washed with dimethylformamide (3×), dichloromethane (3×), methanol/dichloromethane (3×) and dried to yield resin 329.

Step G. Synthesis of 330. Resin 329 was elaborated on an ABI automated peptide synthesizer, utilizing standard HBTU/HoBt couplings of the FMOC-protected amino acids with DIEA as base in NMP, and FMOC deprotections using piperidine in NMP. Then the methyl ester was hydrolyzed by treating the resin (300 mg) with KOTMS (200 mg)/THF (3 mL) for 2 h, filtered, washed with NMP (2×), methanol (3×), and dichloromethane (3×). After drying the resin (200 mg) was stirred in a solution containing PyBrop (300 mg), aziridine carboxylic acid, methyl ester (2.1 g) and DIEA in (0.5 mL) in DMA (2 mL). The reaction was vortexed overnight and the resin was collected and dried. Treatment of the resin with 95% aqueous trifluoroacetic acid/dichloromethane/ethanol, 2:2:1 for 1 h, followed by filtration and concentration afforded 331.

Step I. Synthesis of Compound 1. A solution of 331 (20 mg) in acetonitrile (2 mL) was treated with a solution of DMP (138 mg) and t-butanol (81 mg) in dichloromethane (2 mL) and stirred overnight. The reaction was treated with a 1:1 mixture of acetonitrile/water (3 mL) followed by water (2 mL). The resulting mixture was filtered and the top layer of filtrate was evaporated with a stream of nitrogen. Preparative HPLC afforded 1 as a colorless solid (5 mg).

Other compounds of this invention may be synthesized using similar techniques with appropriate modifications. Such modifications would be readily apparent to those of skill in the art.

EXAMPLE 2

Inhibition of HCV NS3 Serine Protease

Insofar as compounds of formula (I) are able to inhibit NS3 serine protease, they are of evident clinical utility for the treatment of viral diseases, including HCV. The compounds of this invention are tested for their ability to inhibit HCV in the following spectrophotometric assay.

The spectrophotometric assays were run in a 96-well microtiter plate at 30° C., using a SpectraMax 250 reader (Molecular Devices, Sunnyvale, Calif.) with kinetic capability. Cleavage of EDVVAbuC-p-nitroanilide (5A-pNA) substrate was performed with or without NS4A in the same buffer used for HPLC assays at 30° C., and pNA release was monitored at 405 nm. The extinction coefficient of p-nitroaniline is independent of pH at values of 5.5. and above [H. Tuppy et al., *Hoppe-Seyler's Z. Physiol. Chem.*, 329, pp. 278-288 (1962); unpublished observations]. The percentage of DMSO did not exceed 4% in these assays.

Determination of the pH dependence of $V_{max}$, $K_m$ and $V_{max}/K_m$ was performed using a series of constant ionic strength buffers containing 50 mM MES, 25 nM Tris, 25 mM ethanolamine and 0.1 M NaCl [J. F. Morrison et al., *Biochemistry*, 27, pp. 5499-5506 (1988)]. The inflection point for log V data was calculated by nonlinear least squares fit of the data to the equation.

$$\log v = \log [V_{max}/(1+H/K_a)]$$

[M. Dixon, et al., *Enzymes*; Academic Press: New York; Vol., pp 138-164 (1979)]. The inflection points for log (V/K) data were calculated by nonlinear least squares fit of the data to the equation:

$$\log v = \log [V_{max}/(1+H/K_a+K_b/H)]$$

[M. Dixon et al., *Enzymes*; Academic Press: New York; Vol., pp. 138-164 (1979)]. The program KineTic (BioKin Ltd) was used in both cases.

Kinetic constants for the rapid equilibrium ordered bisubstrate reaction were determined from rate vs. [4A], [EDVV AbuC-pNA] data by non-linear least squares fitting to equation 1 [J. F. Morrison, *Biochim. Biophys. Acta.*, 185, pp. 269-286 (1969)] as described in the text. $K_{ii}$ and $K_{is}$ values for peptidyl inhibitors were determined from rate vs. [inhibitor], [substrate] data and fitting to the equation for mixed inhibition:

$$\text{rate} = V_{max}[S]/\{K_m(1+[I]/K_{is})+[S](1+[I]/K_{ii})\}$$

The commercial program KinetAsyst (StateCollege, Pa.) was used for both procedures. Ki values were calculated from rate vs. [inhibitor] plots by a nonlinear least squares fit of the data to the equation of Morrison for tight binding competitive inhibition [J. F. Morrison, *Biochim. Biophys. Acta.*, 185, pp. 269-286 (1969)]. The KineTic program (BioKin Ltd) was used for this procedure.

The results are shown in Table 2. $K_i$ values are expressed in μM. Category "A" indicates <1 μM inhibition; category "B" indicates 1-100 μM inhibition; category "C" indicates >100 μM. The designation "ND" indicates that the compound was not tested.

TABLE 2

Enzyme inhibition data for compounds 1-9.

| Compound | $K_i$ |
|---|---|
| 1 | A |
| 2 | ND |
| 3 | ND |
| 4 | ND |
| 5 | ND |
| 6 | ND |
| 7 | A |
| 8 | ND |
| 9 | A |

While we have hereinbefore presented a number of embodiments of this invention, it is apparent that my basic construction can be altered to provide other embodiments which utilize the methods of this invention. Therefore, it will be appreciated that the scope of this invention is to be defined by the claims appended hereto rather than the specific embodiments which have been presented hereinbefore by way of example.

We claim:

1. A compound of the formula (I):

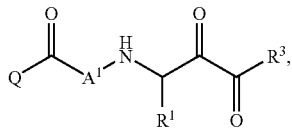

(I)

wherein:

$R^1$ is selected from $(C_1$-$C_6)$-straight or branched alkyl, or $(C_2$-$C_6)$-straight or branched alkenyl or alkynyl, wherein up to 4 hydrogen atoms in $R^1$ are optionally and independently replaced with a halogen; and wherein any hydrogen atom bound to any terminal carbon atom in $R^1$ is optionally and independently replaced with —SH or —OH;

$R^3$ is selected from

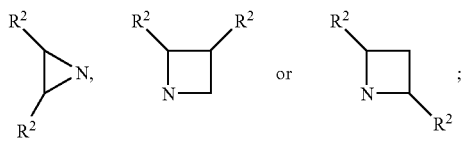

wherein each $R^2$ is independently selected from —$R^{11}$, —Ar, —O—$R^{11}$, —O—Ar, —O—$R^{11}$—Ar, $R^{11}$—C(O)—$R^{11}$, —N($R^{11}$)$_2$, —N($R^{11}$)—C(O)O—$R^{11}$, —N($R^{11}$)—C(O)O—$R^{11}$—Ar, —C(O)O—$R^{11}$, —O—C(O)—N($R^{11}$)$_2$, halo, —CN, —NO$_2$, —$R^{11}$—C(O)—$R^{11}$, —$R^{11}$—C(O)O—$R^{11}$, —O—C(O)—$R^{11}$, —C(O)—N($R^{11}$)$_2$, —C(O)—N($R^{11}$)—Ar, —N($R^{11}$)—C(O)—$R^{11}$, —$R^{11}$—C(O)—N($R^{11}$)$_2$, —S(O)$_2$—$R^{11}$, or —S(O)$_2$—N($R^{11}$)$_2$;

wherein up to 2 hydrogen atoms in $R^2$ are optionally and independently replaced with a different moiety selected from —$R^{11}$, —Ar, —O—$R^{11}$, —O—Ar, —O—$R^{11}$—Ar, —$R^{11}$—C(O)—$R^{11}$, —NH—($R^{11}$)$_2$, —N($R^{11}$)—C(O)O—$R^{11}$, —N($R^{11}$)—C(O)O—$R^{11}$—Ar, —C(O)O—$R^{11}$, —O—C(O)—N($R^{11}$)$_2$, halo, —CN, —NO$_2$, —$R^{11}$—C(O)—$R^{11}$, —$R^{11}$—C(O)O—$R^{11}$, —O—C(O)—$R^{11}$, —C(O)—N($R^{11}$)$_2$, —C(O)—N($R^{11}$)—Ar, —N($R^{11}$)—C(O)—$R^{11}$, —$R^{11}$—C(O)—N($R^{11}$)$_2$, —S(O)$_2$—$R^{11}$, or —S(O)$_2$—N($R^{11}$)$_2$;

wherein each $R^{11}$ is independently selected from hydrogen, $(C_1$-$C_6)$-straight or branched alkyl or $(C_2$-$C_6)$-straight or branched alkenyl or alkynyl; and wherein up to 3 hydrogen atoms in said alkyl, alkenyl or alkynyl are optionally and independently replaced with halo;

each Ar is a monocyclic, bicyclic or tricyclic ring system wherein in said ring system:

(a) each ring is independently partially unsaturated or fully saturated;

(b) each ring comprises 3 to 7 ring atoms independently selected from C, N, O or S;

(c) no more than 4 ring atoms in Q are selected from N, O or S; and (d) any S is optionally replaced with S(O) or S(O)$_2$;

wherein up to 3 hydrogen atoms in each Ar is optionally and independently replaced with a moiety selected from —$R^{11}$, —Ar, —O—$R^{11}$, —O—Ar, —N($R^{11}$)$_2$, —N($R^{11}$)—Ar, —C(O)O$R^{11}$, —C(O)O—Ar, —C(O)—N($R^{11}$)$_2$, —O—C(O)—N($R^{11}$)$_2$, —CN, —NO$_2$, —S$R^{11}$, or —S—Ar; and wherein when a hydrogen atom in Ar is replaced with a first moiety comprising Ar, said first moiety is not substituted with a second moiety comprising Ar;

$A^1$ is selected from a bond, —NH—C($R^4$)—C(O)—, or

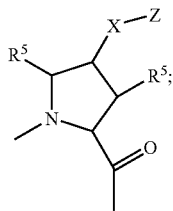

wherein X is selected from a bond, —O—, —NR—, —C(R)$_2$—, —C(O)—, —C(R)$_2$—C(R)$_2$—, —C(R)$_2$—C(R)$_2$—C(R)$_2$—, —C(R)=C(R)—, —CH(R)—O—, —C(R)—N(R)—, —C(R)$_2$—C(O)—, —O—C(R)$_2$—, —N(R)—C(R)$_2$—, —O—C(O)—, —N(R)—C(O)—, —C(O)—C(R)$_2$—, —C(O)—N(R)—, —C(O)—O—, —O—N(R)—, —N(R)—O—, —N(R)—N(R)—, or —N=N—; wherein each R is independently selected from —$R^{11}$, —Ar, —$R^{11}$—Ar, —C(O)O—$R^{11}$, —C(O)—N($R^{11}$)$_2$, —O—$R^{11}$, —O—Ar, halo, —CN, —NO$_2$, —N($R^{11}$)$_2$, —N($R^{11}$)—Ar, —S(O)$_2$—$R^{11}$, or —S(O)$_2$—N($R^{11}$)$_2$;

Z is selected from —$R^{11}$, —Ar, or —$R^{11}$—Ar;

$R^4$ is selected from —$R^{11}$, —Ar, —$R^{11}$—Ar, —C(O)O—Ar, or —O—C(O)—N($R^{11}$)$_2$, wherein up to 3 hydrogen atoms in $R^4$ are optionally and independently replaced with a different moiety selected from —$R^{11}$, —Ar, —O—$R^{11}$, —O—Ar, —O—$R^{11}$—Ar, —$R^{11}$—C(O)—$R^{11}$, —N—($R^{11}$)$_2$, —N($R^{11}$)—C(O)O—$R^{11}$, —C(O)—N($R^{11}$)$_2$, —N($R^{11}$)—C(O)O—

R¹¹—Ar, —C(O)O—R¹¹, —O—C(O)—N(R¹¹)₂, halo, —CN, —NO₂, —R¹¹—C(O)O—R¹¹, —S(O)₂R¹¹, or —S(O)₂—N(R¹¹)₂;

each $R^5$ is independently selected from —R¹¹, —Ar, —C(O)O—R¹¹, —C(O)O—Ar, —O—C(O)—N(R¹¹)₂, —O—C(O)—N(R¹¹)—Ar, —C(O)—N(R¹¹)₂, —C(O)—N(R¹¹)—Ar, —O—R¹¹, halo, —CN, —NO₂, —N(R¹¹)₂ or —S(O)₂—R¹¹;

or wherein —X-Z and one $R^5$ are taken together with the carbon atoms to which they are respectively bound to form a 5 to 7-membered ring comprising 0 to 3 heteroatoms independently selected from O, N, or S;

Q is selected from —OR⁶, —N(R⁶)₂, R¹¹, —R¹¹—O—R¹¹, —R¹¹—NH₂, —Ar, A³—NH—C(R⁷)—, or —A³; wherein each $R^6$ is independently selected from R¹¹, —R¹¹—O—R¹¹, —R¹¹—NH₂, —R¹¹—Ar, or —Ar; and $R^7$ is selected from —R¹¹ or —Ar;

$A^3$ is selected from R⁶, R⁸—C(O)—, R⁸—S(O)₂—, R⁶—C(O)—NH—C(R⁶)—C(O)— or R⁶—NH—C(R⁶)—C(O)—; and $R^8$ is selected from —R⁶, —OR⁶, or —N(R⁶)₂.

2. The compound according to claim 1, wherein:
Q is A³—NH—CH(R⁷)—; and
$A^3$ is selected from R⁶—C(O)—NH—CH(R⁶)—C(O)—, R⁸—C(O)— or R⁸—S(O)₂—.

3. The compound according to claim 2, wherein Q is A³—NH—CH(CH(CH₃)₂)—;
$A^3$ is selected from Ar—C(O)—NH—CH(CH(CH₃)₂)—C(O)—, R⁶—O—C(O)—, R⁶—O—S(O)₂, or R⁶—NH—C(O)—; and
$R^6$ is selected from R¹¹—, Ar—R¹¹— or Ar—.

4. The compound according to claim 1, wherein Q is selected from:

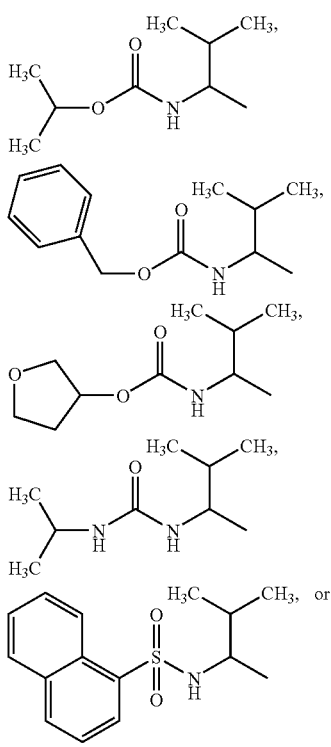

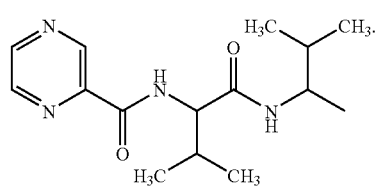

5. The compound according to claim 4, wherein Q is

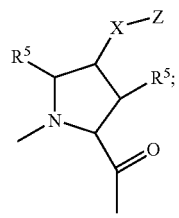

6. The compound according to claim 1, wherein:
$A^1$ is

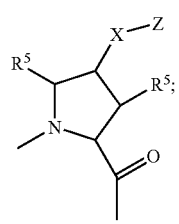

wherein X is —O—C(O)— or a bond;

Z is hydrogen or Ar;

one $R^5$ is hydrogen; and the other $R^5$ is selected from —R¹¹, —Ar, —C(O)O—R¹¹, —C(O)O—Ar, —O—C(O)—N(R¹¹)₂, —O—C(O)—N(R¹¹)—Ar, —C(O)—N(R¹¹)₂, or —C(O)—N(R¹¹)—Ar.

7. The compound according to claim 1, wherein:
$A^1$ is and one $R^5$ is hydrogen; and X, Z and the other $R^5$ are taken together to form an unsubstituted or oxo—substituted cyclopentyl moiety.

8. The compound according to claim 6, wherein $A^1$ is selected from:

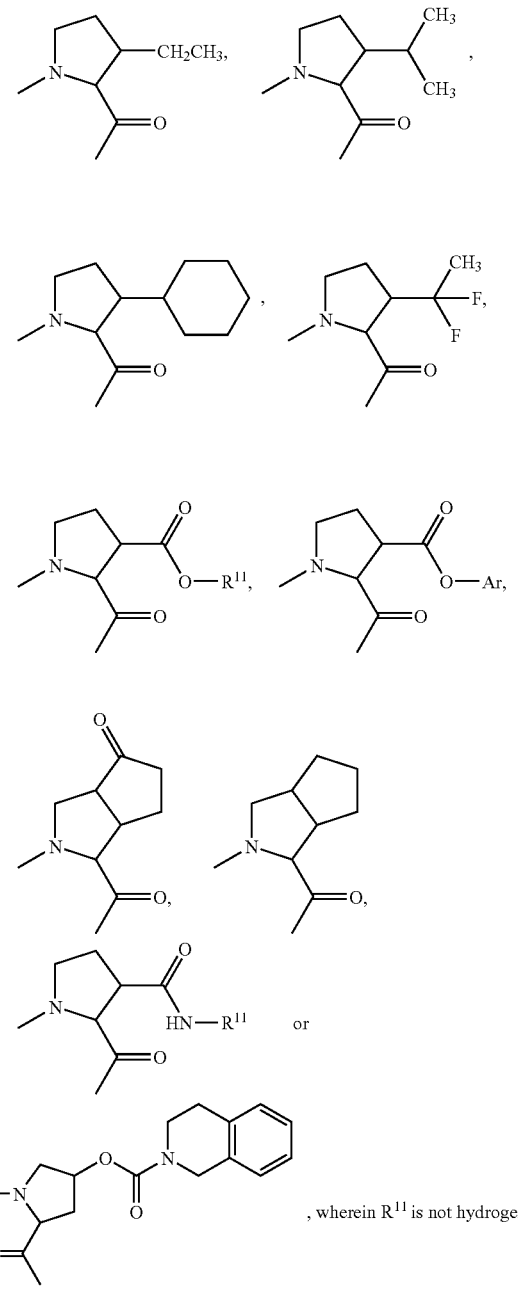

9. The compound according to claim 8, wherein $A^1$ is

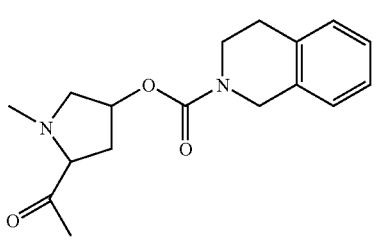

10. The compound according to claim 7, wherein $A^1$ is selected from

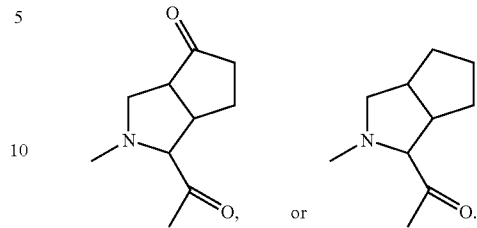

11. The compound according to claim 1, wherein $R^1$ is a straight chain alkyl moiety.

12. The compound according to claim 11, wherein $R^1$ is n-propyl.

13. The compound according to claim 1, wherein in the $R^3$ moiety, one $R^2$ is hydrogen and the other $R^2$ moiety is selected from $R^{11}$, C(O)—O—$R^{11}$, Ar or —OAr.

14. compound according to claim 13, wherein one $R^2$ is hydrogen and the other $R^2$ moiety is selected from hydrogen, methyl, C(O)—OH, C(O)—O—$CH_3$, C(O)—O—C($CH_3$)$_3$, phenyl or phenoxy.

15. The compound according to claim 1, wherein said compound has the formula (II):

(II)

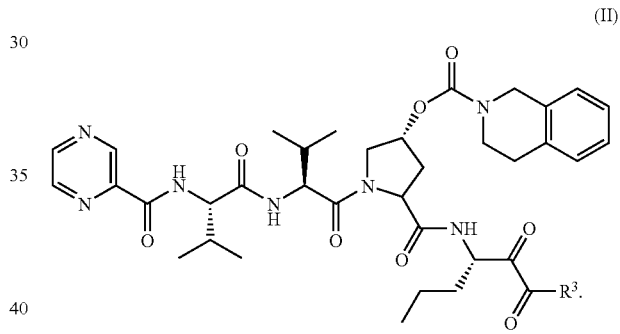

16. A composition comprising a compound according to claim 1 or a pharmaceutically acceptable salt, derivative or prodrug thereof; and a acceptable carrier, adjuvant or vehicle.

17. The composition according to claim 16, wherein said composition comprises an additional agent selected from α-, β-, or γ-interferon, ribavarin, or amantadine.

18. A method of inhibiting the activity of a serine protease in vitro comprising the step of contacting said serine protease with a compound according to claim 1.

19. The method according to claim 18, wherein said protease is an HCV NS3 protease.

20. A method of treating an HCV infection in a patient comprising the step of administering to said patient a composition according to claim 16.

21. The method according to claim 20, comprising the additional step of administering to said patient an additional agent selected from α-, β-, or γ-interferon, ribavarin, or amantadine; wherein said additional agent is administered to said patient as part of said composition according to claim 16 or as a separate dosage form.

22. A pharmaceutical composition comprising a compound according to any one of claims 1-15 and a pharmaceutically acceptable carrier, adjuvant, or vehicle.

* * * * *